US011904170B2

(12) United States Patent
Zenisek et al.

(10) Patent No.: US 11,904,170 B2
(45) Date of Patent: Feb. 20, 2024

(54) PATIENT-LEARNED CONTROL OF MEDICAL DEVICE

(71) Applicant: Medtronic, Inc., Minneapolis, MN (US)

(72) Inventors: Todd D. Zenisek, Georgetown, TX (US); Touby A. Drew, Golden Valley, MN (US); Brian Andrew Smith, Apple Valley, MN (US); Juan G. Hincapie, Maple Grove, MN (US); Leonid M. Litvak, Los Angeles, CA (US)

(73) Assignee: Medtronic, Inc., Minneapolis, MN (US)

( * ) Notice: Subject to any disclaimer, the term of this patent is extended or adjusted under 35 U.S.C. 154(b) by 48 days.

(21) Appl. No.: 17/456,327

(22) Filed: Nov. 23, 2021

(65) Prior Publication Data
US 2022/0226658 A1 Jul. 21, 2022

Related U.S. Application Data

(60) Provisional application No. 63/212,988, filed on Jun. 21, 2021, provisional application No. 63/140,115, filed on Jan. 21, 2021.

(51) Int. Cl.
| | |
|---|---|
| *A61N 1/36* | (2006.01) |
| *A61N 1/372* | (2006.01) |
| *A61N 1/05* | (2006.01) |

(52) U.S. Cl.
CPC ....... *A61N 1/36135* (2013.01); *A61N 1/0534* (2013.01); *A61N 1/0551* (2013.01); *A61N 1/0568* (2013.01); *A61N 1/37235* (2013.01); *A61N 1/36067* (2013.01); *A61N 1/36082* (2013.01)

(58) Field of Classification Search
CPC .............. A61N 1/36135; A61N 1/0534; A61N 1/0551; A61N 1/0568; A61N 1/37235
See application file for complete search history.

(56) References Cited

U.S. PATENT DOCUMENTS

| | | |
|---|---|---|
| 8,150,531 B2 | 4/2012 | Skelton |
| 8,396,565 B2 | 3/2013 | Singhal et al. |
| 9,919,159 B2 | 3/2018 | Skelton et al. |
| 10,449,371 B2 | 10/2019 | Serrano Carmona |
| 10,576,282 B2 | 3/2020 | Doan et al. |
| 10,610,688 B2 | 4/2020 | Thakur et al. |

(Continued)

OTHER PUBLICATIONS

International Search Report and Written Opinion of International Application No. PCT/US2021/072590, dated Mar. 21, 2022, 11 pp.

*Primary Examiner* — Joseph M Dietrich
(74) *Attorney, Agent, or Firm* — Shumaker & Sieffert, P.A.

(57) ABSTRACT

A system for selecting a sensitivity level for adjusting an intensity setting for therapy provided to a patient includes one or more processors and one or more processors coupled to the memory. The one or more processors are configured to receive an indication of an input to adjust an intensity setting related to the therapy provided to the patient and determine a sensitivity level for adjustment of the intensity setting based on an efficacy of the therapy provided to the patient. The one or more processors are further configured to determine an updated intensity level for the intensity setting based on the sensitivity level and the input to adjust the intensity setting and output an instruction to cause a medical device to provide the therapy at the updated intensity level.

20 Claims, 5 Drawing Sheets

(56) References Cited

U.S. PATENT DOCUMENTS

| | | |
|---|---|---|
| 10,806,344 B2 | 10/2020 | Goetz |
| 10,864,368 B2 | 12/2020 | Stanslaski et al. |
| 2007/0255118 A1 | 11/2007 | Miesel et al. |
| 2018/0085584 A1 | 3/2018 | Thakur et al. |
| 2018/0207432 A1 | 4/2018 | Thacker et al. |
| 2019/0099602 A1 | 4/2019 | Esteller et al. |
| 2019/0381320 A1 | 12/2019 | Bradley et al. |

PATIENT-LEARNED CONTROL OF MEDICAL DEVICE

This application claims priority to U.S. Provisional Patent Application No. 63/212,988, filed Jun. 21, 2021 and U.S. Provisional Patent Application No. 63/140,115, filed Jan. 21, 2021, each of which is incorporated herein by reference.

TECHNICAL FIELD

This disclosure generally relates to medical devices.

BACKGROUND

Medical devices (e.g., an implantable medical device or an external medical device) may include electrical stimulation devices, drug pumps, insulin pumps, or cardiac stimulation devices. Electrical stimulation devices, for example, neurostimulators or neurostimulation devices, may be external to or implanted within a patient, and configured to deliver electrical stimulation therapy to various tissue sites to treat a variety of symptoms or conditions such as chronic pain, tremor, Parkinson's disease, epilepsy, or other neurological disorders, urinary or fecal incontinence, sexual dysfunction, obesity, or gastroparesis. An electrical stimulation device may deliver electrical stimulation therapy via electrodes, e.g., carried by one or more leads, positioned proximate to target locations associated with the brain, the spinal cord, pelvic nerves, tibial nerves, peripheral nerves, the gastrointestinal tract, or elsewhere within a patient. Stimulation proximate the spinal cord, proximate the sacral nerve, within the brain, and proximate peripheral nerves is often referred to as spinal cord stimulation (SCS), sacral neuromodulation (SNM), deep brain stimulation (DBS), and peripheral nerve stimulation (PNS), respectively.

SUMMARY

In general, this disclosure describes techniques for patient-learned control of medical devices. The medical devices may be implantable and/or wearable and may be configured to provide one or more of deep brain stimulation (DBS), spinal cord stimulation (SCS), sacral neuromodulation (SNM), and peripheral nerve stimulation (PNS), targeted drug delivery (TDD), or another therapy. For example, a medical device (e.g., an external programmer) may be configured to help a patient provide input to adjust an intensity setting set by a clinician. For example, the device may provide a "therapy knob" that adjusts the intensity setting based on one or more adjustment parameters (e.g., a mode of the external device, an efficacy of therapy, etc.). Intensity may be a function of amplitude, pulse width, and/or frequency. For example, the medical device may apply electrical stimulation at a voltage or current based on a position of the therapy knob and the intensity setting.

If the device is in a training or trial mode, the device may determine that an input to change an intensity using the therapy knob (e.g., one notch) may result in larger adjustments than when the external device is in chronic mode. In some examples, the device may set the sensitivity of the therapy knob (e.g., by how much intensity changes) based on an efficacy of the therapy provided to the patient (e.g., an activity level of the patient). For example, the device may set the sensitivity of the therapy knob to a relatively high sensitivity level when the activity level of the patient corresponds to walking and a relatively low sensitivity level when the activity level of the patient corresponds to the patient laying down. In this way, a system may help to provide patient control measures that simplify or make changes to a therapy easier for a patient, which may improve a therapy provided to the patient. Moreover, patient control measures may reduce a number of times that a clinician sets an intensity level for therapy, which may help to reduce an amount of time a clinician spends configuring medical devices.

In one example, this disclosure is directed to a system for selecting a sensitivity level for adjusting an intensity setting for therapy provided to a patient. The system comprises one or more processors and one or more processors coupled to the memory. The one or more processors are configured to receive an indication of an input to adjust an intensity setting related to the therapy provided to the patient and determine a sensitivity level for adjustment of the intensity setting based on an efficacy of the therapy provided to the patient. The one or more processors are further configured to determine an updated intensity level for the intensity setting based on the sensitivity level and the input to adjust the intensity setting and output an instruction to cause a medical device to provide the therapy at the updated intensity level.

In another example, this disclosure is directed to a method for selecting a sensitivity level for adjusting an intensity setting for therapy provided to a patient. The method includes receiving, by one or more processors, an indication of an input to adjust an intensity setting related to the therapy provided to the patient and determining, by the one or more processors, a sensitivity level for adjustment of the intensity setting based on an efficacy of the therapy provided to the patient. The method further includes determining, by the one or more processors, an updated intensity level for the intensity setting based on the sensitivity level and the input to adjust the intensity setting; and outputting, by the one or more processors, an instruction to cause a medical device to provide the therapy at the updated intensity level.

In one example, this disclosure is directed to an external programmer for adjusting an intensity setting for therapy provided to a patient. The external programmer comprising one or more processors configured to receive an indication of an input to adjust an intensity setting related to the therapy provided to the patient and determine a sensitivity level for adjustment of the intensity setting based on an efficacy of the therapy provided to the patient. The one or more processors are further configured to determine an updated intensity level for the intensity setting based on the sensitivity level and the input to adjust the intensity setting and output an instruction to cause a medical device to provide the therapy at the updated intensity level.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

The techniques of this disclosure may include an external device (e.g., an external programmer and/or a remote client) configured to help a patient provide input to adjust an intensity setting set by a clinician. For example, the external device may provide a "therapy knob" that adjusts a sensitivity level of the therapy knob based on one or more adjustment parameters (e.g., a mode of the external device, an efficacy of therapy, etc.). Intensity may be a function of amplitude, pulse width, and/or frequency. For example, if the external device is in a training or trial mode, an input to change an intensity using the therapy knob (e.g., one notch) may result in larger adjustments than when the external device is in chronic mode. In some examples, the external device may set the sensitivity of the therapy knob based on an activity level of the patient. The sensitivity of the therapy knob may refer to the amount by which the intensity changes per unit change in the therapy knob (e.g., the amount by the intensity changes every notch of the knob). The knob is one example, and other examples such as push buttons, up/down, right/left arrow buttons, dials, and generally various ways in which to increase or decrease a setting.

The device (e.g., an external device) may set a sensitivity of the therapy knob based on an efficacy of therapy. For deep brain stimulation (DBS), the external device may determine the efficacy of therapy based on an amount of tremor, ambulation, and/or open and closed fist range. In this way, a system may help to provide patient control measures that simplify or make changes to a therapy easier for a patient, which may improve a therapy provided to the patient. Moreover, patient control measures may reduce a number of times that a clinician sets an intensity level for therapy, which may help to reduce an amount of time a clinician spends configuring medical devices. In this way, a system may help to provide patient control measures that simplify or make changes to a therapy easier for a patient, which may improve a therapy provided to the patient.

Techniques described herein may be directed to implantable medical devices and external medical devices. Examples described herein may describe techniques with reference to medical devices, however, aspects of such techniques may apply to any medical device. Again, examples of medical devices, which may be external or implantable), may include drug pumps, insulin pumps, or cardiac stimulation devices.

Figure 1:
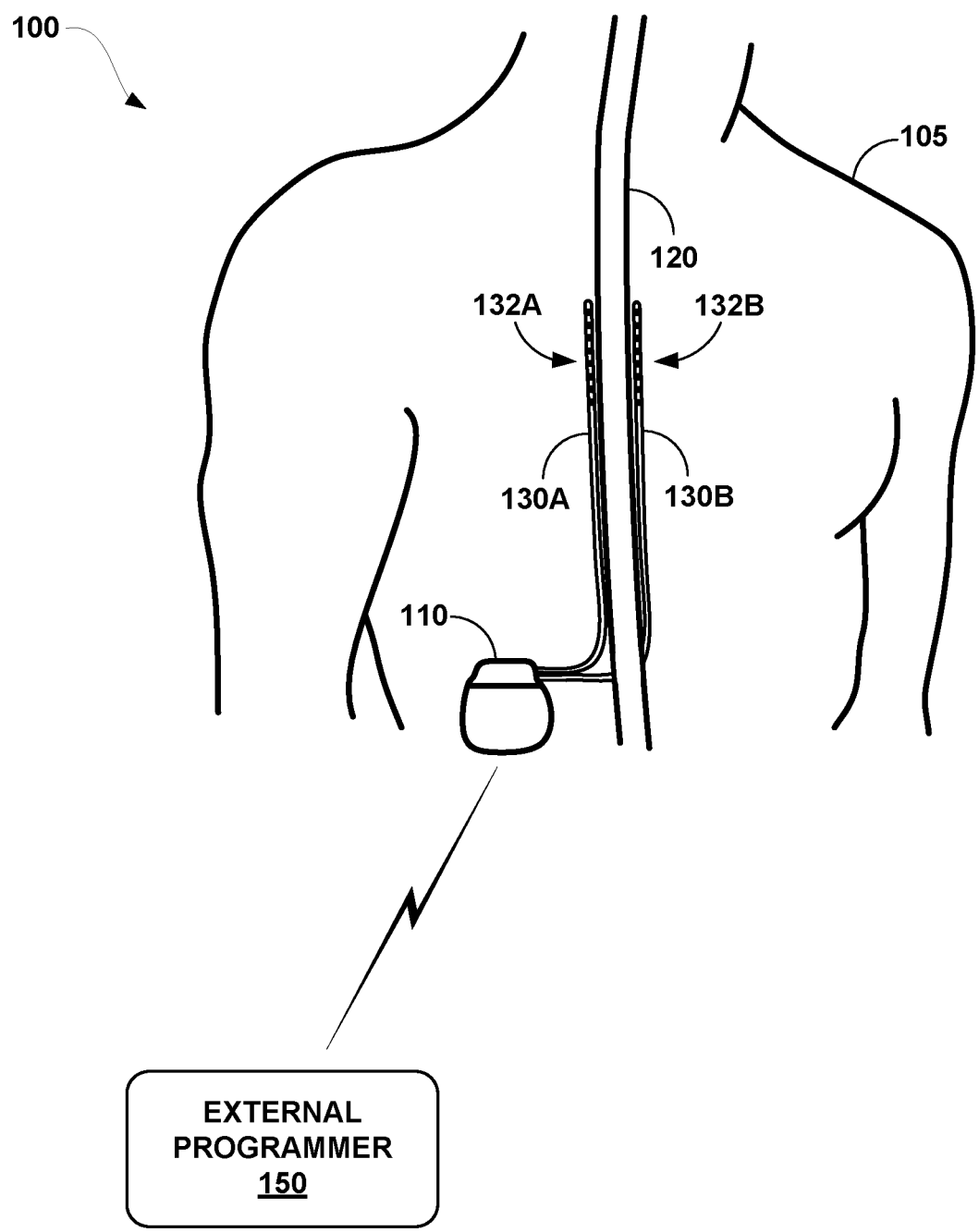
FIG. 1 is a conceptual diagram illustrating an example system that includes an implantable medical device (IMD) in the form of a neurostimulation device configured to deliver spinal cord stimulation (SCS) and an external programmer, in accordance with one or more techniques of this disclosure.

FIG. 1 is a conceptual diagram illustrating an example system 100 that includes an implantable medical device (IMD) 110 configured to deliver SCS therapy, processing circuitry 140, and an external programmer 150, in accordance with one or more examples of this disclosure. Although the examples described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of stimulation.

External programmer 150 may be configured to provide patient information to support techniques for identifying problem patients, whose patient information should potentially be prioritized for determination of patient treatment or patient communication. In some examples, external programmer 150 may help to cause IMD 110 to perform a diagnostic test, for example, to capture patient data in response to identifying patient 105 as a problem patient. External programmer 150 may use a communication mode that is selected based on patient information, which may help to prioritize a delivery of data between patient 105 and a clinician. External programmer 150 may facilitate a scheduling of a patient interaction, for example, to capture patient data in response to identifying patient 105 as a problem patient. External programmer 150 may provide a therapy knob that adjusts a sensitivity level of the therapy knob based on one or more adjustment parameters (e.g., a mode of the external device, an efficacy of therapy, etc.).

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105, e.g., for relief of chronic pain or other symptoms, or restoration or support of physical function or control in the case of spinal cord injury or degeneration, via one or more electrodes 132A, 132B of leads 130A and/or 130B, respectively. In the example of FIG. 1, each lead 130A, 130B includes eight electrodes 132A, 132B respectively, although the leads may each have a different number of electrodes. Leads 130A, 130B may be referred to collectively as "leads 130" and electrodes 132A, 132B may be referred to collectively as electrodes 132. In other examples, IMD 110 may be coupled to a single lead carrying multiple electrodes or more than two leads each carrying multiple electrodes.

IMD 110 may be a chronic electrical stimulator that remains implanted within patient 105 for weeks, months, or years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to one or more leads percutaneously implanted within the patient. In some examples, IMD 110 uses electrodes on one or more leads, while in other examples, IMD 110 use one or more electrodes on a lead or leads and one of more electrodes on a housing of the IMD. In further examples, IMD 110 may be leadless and instead use only electrodes carried on a housing of IMD.

IMD 110 may be constructed of any polymer, metal, or composite material sufficient to house the components of IMD 110 (e.g., components illustrated in FIG. 2) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted at other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

In the example of FIG. 1, electrical stimulation energy, which may be delivered as regulated current or regulated voltage-based pulses, is delivered from IMD 110 to one or more target tissue sites of patient 105 via leads 130 and electrodes 132. Leads 130 position electrodes 132 adjacent to target tissue of spinal cord 120. One or more of the electrodes 132 may be disposed at a distal tip of a lead 130 and/or at other positions at intermediate points along the lead. Leads 130 may be implanted and coupled to IMD 110. The electrodes 132 may transfer electrical stimulation generated by an electrical stimulation generator in IMD 110 to tissue of patient 105. Although leads 130 may each be a single lead, a lead 130 may include a lead extension or other segments that may aid in implantation or positioning of lead 130.

The electrodes of leads 130 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration. Deployment of electrodes via leads 130 is described for purposes of illustration, but electrodes may be arranged on a housing of IMD 110, e.g., in rows and/or columns (or other arrays or patterns), as surface electrodes, ring electrodes, or protrusions.

Stimulation parameters defining the electrical stimulation pulses delivered by IMD 110 through electrodes 132 of leads 130 may include information identifying which electrodes have been selected for delivery of the stimulation pulses according to a stimulation program and the polarities of the selected electrodes (the electrode combination), and voltage or current amplitude, pulse rate (e.g., frequency), and pulse width of the stimulation pulses. The stimulation parameters may further include a cycle parameter that specifies when, or how long, stimulation is turned on and off. Stimulation parameters may be programmed prior to delivery of the stimulation pulses, manually adjusted based on user input, or automatically controlled during delivery of the stimulation pulses, e.g., based on sensed conditions.

Although the example of FIG. 1 is directed to SCS therapy, e.g., to treat pain or restore or support physical function or control in the case of spinal cord injury or degeneration, in other examples, system 100 may be configured to treat other conditions that may benefit from stimulation therapy. For example, system 100 may be used to treat tremor, Parkinson's disease, epilepsy, or other neurological disorders, urinary or fecal incontinence, sexual dysfunction, obesity, or gastroparesis, or psychiatric disorders such as depression, mania, obsessive compulsive disorder, or anxiety disorders. Hence, in some examples, system 100 may be configured to deliver SNM, DBS, PNS, or other stimulation, such as peripheral nerve field stimulation (PNFS), cortical stimulation (CS), gastrointestinal stimulation, or any other stimulation therapy capable of treating a condition of patient 105.

Leads 130 may include, in some examples, one or more sensors configured to sense one or more physiological parameters of patient 105, such as patient activity, pressure, temperature, or other characteristics. At least some of electrodes 132 may be used to sense electrical signals within patient 105, additionally or alternatively to delivering stimulation. IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation. In some examples, the target tissue includes nerves, smooth muscle or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical or lumbar regions.

Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may reduce the perception of pain by patient 105, and thus, provide efficacious therapy results. In some examples, some electrical stimulation pulses may be directed to glial cells while other electrical stimulation (e.g., delivered by a different electrode combination) is directed to neurons. In other examples, electrical stimulation pulses may be directed to restore a function lost due to a spinal cord injury.

IMD 110 may generate and may deliver electrical stimulation therapy to a target stimulation site within patient 105 via the electrodes of leads 130 to patient 105 according to one or more therapy stimulation programs. A therapy stimulation program specifies values for one or more parameters that define an aspect of the therapy delivered by IMD 110 according to that program. For example, a therapy stimulation program that controls delivery of stimulation by IMD 110 in the form of stimulation pulses may define values for voltage or current pulse amplitude, pulse width, and pulse rate (e.g., pulse frequency) for stimulation pulses delivered by IMD 110 according to that program, as well as the particular electrodes and polarities forming an electrode combination used to deliver the stimulation pulses.

A user, such as a clinician, caretaker, or patient 105, may interact with a user interface of an external programmer 150 to program IMD 110. External programmer 150 may represent a physician programmer or patient programmer. Programming of IMD 110 may refer generally to the generation and transfer of commands, programs, or other information to control the operation of IMD 110. In this manner, IMD 110 may receive the transferred commands and programs from external programmer 150 to control electrical stimulation therapy. External programmer 150 may transmit therapy stimulation programs, program groups, stimulation parameter adjustments, therapy stimulation program selections, user input, or other information to control the operation of IMD 110, e.g., by wireless telemetry or wired connection.

External programmer 150 may perform a stimulation parameter adjustment that changes a set of stimulation parameters of an existing program. For example, external programmer 150 may automatically, semi-automatically, or based on a user selection, may determine or more stimulation parameter adjustments for an existing program. In this example, external programmer 150 may pass through the one or more parameter adjustments for the existing program. For instance, external programmer 150 may determine a parameter adjustment (e.g., receive the adjustment from a user input from a health professional) that sets an intensity value of a particular stimulation parameter of a program and may relay the parameter adjustment to IMD 110.

External programmer 150 may be characterized as a physician or clinician programmer if external programmer 150 is primarily intended for use by a physician or clinician. In other cases, external programmer 150 may be characterized as a patient programmer if external programmer 150 is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change stimulation therapy. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

IMD 110 and external programmer 150 may exchange information and may communicate via wireless communication. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

IMD 110, in response to commands from external programmer 150, may deliver electrical stimulation therapy according to one or more therapy stimulation programs, or a group of programs to a target tissue site of the spinal cord 120 of patient 105 via electrodes 132 on leads 130. In some examples, IMD 110 automatically modifies therapy stimulation programs as therapy needs of patient 105 evolve over time. For example, the modification of the therapy stimulation groups or programs may cause the adjustment of at least one parameter of the plurality of stimulation pulses.

In accordance with the techniques of the disclosure, external programmer 150 (e.g., an external patient programmer) may help a patient provide input to adjust an intensity setting set by a clinician. For example, external programmer 150 may provide a "therapy knob" that adjusts the intensity setting based on one or more adjustment parameters (e.g., a mode of the external device, an efficacy of therapy, etc.). Intensity may be a function of amplitude, pulse width, and/or frequency. For example, if IMD 110 is in a training or trial mode, an input to change an intensity using the therapy knob (e.g., one notch) may result in larger adjustments than when IMD 110 is in chronic mode. The amount by which intensity changes per input (e.g., per change in position by one notch for therapy knob) may be referred to as the sensitivity of the therapy knob. In some examples, external programmer 150 may set the sensitivity of the therapy knob based on an activity level of the patient. The external programmer 150 may instruct IMD 110 to provide therapy using the intensity setting.

While examples refer to a specific type of rotary control element, a "knob," to select an intensity setting, techniques described herein may apply to other rotary control elements, and other types of control elements, such as, for example, a linear control element (e.g., a dial). Such control elements may be physical (e.g., a physical knob or dial) or may be virtual (e.g., a knob or dial illustrated on a display. In some examples, control elements may be implemented using sound (e.g., a voice command) or using motion (e.g., a movement of an external device up or down, an eye movement, an arm movement, or a leg movement).

The disclosure describes examples of adjusting the sensitivity. For instance, external programmer 150 may increase or decrease the amount by which the intensity changes per input from the patient. As an example, for a first sensitivity level, turning the therapy knob by one notch causes the intensity level to increase by a first amount. For a second sensitivity level, turning the therapy knob by one notch causes the intensity level to increase by a second, different amount.

External programmer 150 may set a sensitivity of the therapy knob based on an efficacy of therapy. For DBS, external programmer 150 may determine the efficacy of therapy based on an amount of tremor, ambulation, and/or open and closed fist range. In some examples, external programmer 150 may additionally determine the sensitivity of the therapy knob based on one or more of a current activity level for the patient, an amount of sleep during a period of time for patient 105, a sleep position during a period of time for patient 105, a set of previous therapy parameter adjustments, a pain rating, a set of physiological signals (e.g., ECAP and/or LFP), or a mode of external programmer (e.g., training or trial mode, or chronic mode). In this way, system 100 may help to provide patient control measures that simplify or make changes to a therapy easier for a patient, which may improve a therapy provided to the patient. Moreover, patient control measures may reduce a number of times that a clinician sets an intensity level for therapy, which may help to reduce an amount of time a clinician spends configuring medical devices.

Figure 2:
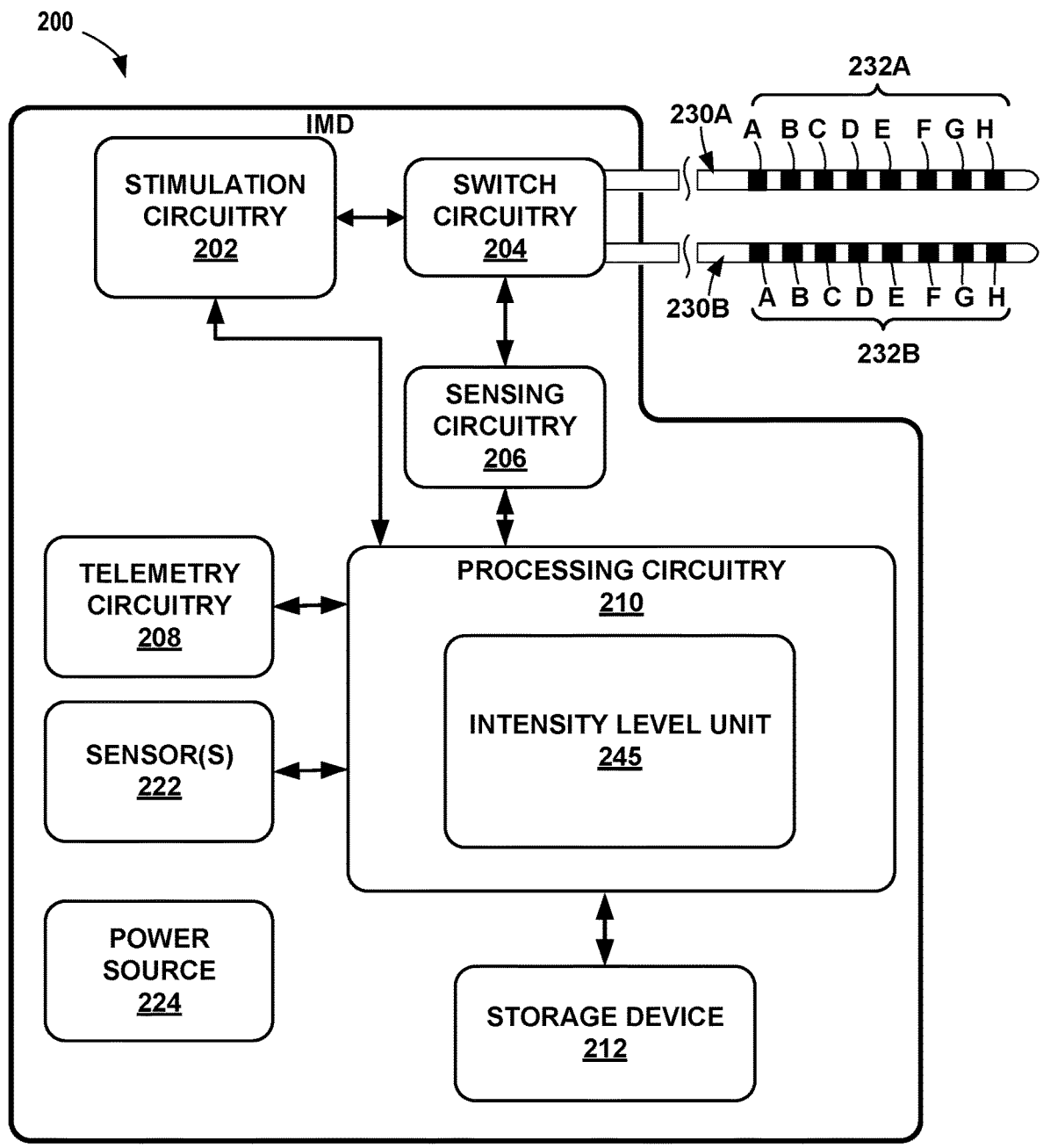
FIG. 2 is a block diagram illustrating an example of an IMD in the form of a stimulation device, in accordance with one or more techniques of this disclosure.

FIG. 2 is a block diagram illustrating an example configuration of components of an IMD 200, in accordance with one or more techniques of this disclosure. IMD 200 may be an example of IMD 110 of FIG. 1. In the example shown in FIG. 2, IMD 200 includes stimulation generation circuitry 202, switch circuitry 204, sensing circuitry 206, telemetry circuitry 208, processing circuitry 210, storage device 212, sensor(s) 222, power source 224, lead 230A carrying electrodes 232A, which may correspond to lead 130B and electrodes 132B of FIG. 1, and lead 230B carrying electrodes 232B, which may correspond to lead 130B and electrodes 132B of FIG. 1.

Stimulation generation circuitry 202 may generate electrical stimulation pulses selected to alleviate symptoms or dysfunction of one or more diseases, disorders, injuries, or syndromes. Intensity level unit 245 may be configured to set an intensity of the electrical stimulation pulses. Intensity may be a function of amplitude, pulse width, and/or frequency of the electrical stimulation pulses. While stimulation pulses are described, stimulation signals may take other forms, such as continuous-time signals (e.g., sine waves) or the like. Each of leads 230A, 230B may include any number of electrodes 232A, 232B. In the example of FIG. 2, each set of electrodes 232A, 232B includes eight electrodes A-H. In some examples, the electrodes are arranged in bipolar combinations. A bipolar electrode combination may use electrodes carried by the same lead 230A, 230B or different leads. For example, an electrode A of electrodes 232A may be a cathode and an electrode B of electrodes 232A may be an anode, forming a bipolar combination.

Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232A, 232B, or directed sensed signals from one or more of electrodes 232A, 232B to sensing circuitry 206. In some examples, each of the electrodes 232A, 232B may be associated with respective regulated current source and sink circuitry to selectively and independently configure the electrode to be a regulated cathode or anode, in which case switch circuitry 204 may not be necessary to direct stimulation signals to electrodes. Instead, current sourced or sunk by selected electrodes may be individually controlled. Stimulation generation circuitry 202 and/or sensing circuitry 206 also may include sensing circuitry to direct electrical signals sensed at one or more of electrodes 232A, 232B.

Sensing circuitry 206 may be configured to monitor signals from any combination of electrodes 232A, 232B. In some examples, sensing circuitry 206 includes one or more amplifiers, filters, and analog-to-digital converters. Sensing circuitry 206 may be used to sense electrophysiological signals. In some examples, sensing circuitry 206 detects electrophysiological signals from a particular combination of electrodes 232A, 232B. In some cases, the particular combination of electrodes for sensing electrophysiological signals includes different electrodes than a set of electrodes 232A, 232B used to deliver stimulation pulses. Alternatively, in other cases, the particular combination of electrodes used for electrophysiological sensing includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

For example, sensing circuitry 206 may be configured to generate sensed condition information. Telemetry circuitry 208 may output the sensed condition information to external programmer 105. Examples of sensed condition information may include accelerometer information indicating an acceleration of medical device 200 along one, two, or three axes, which may represent a acceleration of patient 105. Processing circuitry 210 may determine a current activity level for patient 105 based on the sensed condition information (e.g., accelerometer information).

In some examples, processing circuitry 210 may determine an amount of sleep during a period of time (e.g., a day) for patient 105 based on the sensed condition information (e.g., accelerometer information). For example, processing circuitry 210 may determine that patient 105 is sleeping when the sensed condition information (e.g., accelerometer information) indicates an activity level that is less than a threshold. In some examples, processing circuitry 210 may determine a sleep position during a period of time (e.g., a day) for patient 105 based on the sensed condition information (e.g., accelerometer information).

In some examples, the neurological signals sensed within a brain of patient 105 may reflect changes in electrical current produced by the sum of electrical potential differences across brain tissue. Examples of neurological brain signals include, but are not limited to, bioelectric signals generated from local field potentials (LFP) sensed within one or more regions of brain 120. Electroencephalogram (EEG) signal or an electrocorticogram (ECoG) signal are also examples of bioelectric signals. For example, neurons generate the bioelectric signals, and if measured at depth, it is LFP, if measured on the coretex, it is ECoG, and if on scalp, it is EEG. In this disclosure, the term "oscillatory signal source" is used to describe a signal source that generates bioelectric signals.

One example of the feature of interest (e.g., biomarker) within the LFPs is synchronized beta frequency band (13-33 Hz) LFP activity recorded within the sensorimotor region of the subthalamic nucleus (STN) in Parkinson's disease patients. The source of the LFP activity can be considered as an oscillatory signal source, within the brain of the patient, that outputs an oscillatory electrical voltage signal that is sensed by one or more of electrodes 116 and/or 118. The suppression of pathological beta activity (e.g., suppression or squelching of the signal component of the bioelectric signals generated from the oscillatory LFP signal source that is within the beta frequency band) by both medication and DBS may correlate with improvements in the motor symptoms of patients who have Parkinson's disease.

ECAPs are a measure of neural recruitment because each ECAP signal represents the superposition of electrical potentials generated from a population of axons firing in response to an electrical stimulus (e.g., a stimulation pulse). Changes in a characteristic (e.g., an amplitude of a portion of the signal or area under the curve of the signal) of an ECAP signals occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude). Therefore, a system can determine that the distance between electrodes and nerves has increased or decreased in response to determining that the measured ECAP characteristic value has increased or decreased. For example, if the set of parameter values stays the same and the ECAP characteristic value of amplitude increases, the system can determine that the distance between electrodes and the nerve has decreased.

Sensing circuitry 206 may be configured to generate a set of physiological signals. For example, sensing circuitry 206 may generate an ECAP for patient 105. In some examples, sensing circuitry 206 may generate an LFP for patient 105. Telemetry circuitry 208 may output the set of physiological signals to external programmer 105.

Telemetry circuitry 208 may support wireless communication between IMD 200 and an external programmer (not shown in FIG. 2) or another computing device under the control of processing circuitry 210. Processing circuitry 210 of IMD 200 may receive, as updates to programs, values for various stimulation parameters such as amplitude and electrode combination, from the external programmer via telemetry circuitry 208. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. As shown, processing circuitry 210 may comprise an intensity level unit 245 that may comprise circuitry and/or software instructions. The software instructions associated with intensity level unit 245 may be stored, for example, at storage device 212.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210, such as, for example, instructions associated with intensity level unit 245.

Power source 224 may be configured to deliver operating power to the components of IMD 200. Power source 224 may include a battery and a power generation circuit to produce the operating power. In some examples, the battery is rechargeable to allow extended operation. In some examples, power source 224 may be configured to recharge a battery through proximal inductive interaction between an external charger and an inductive charging coil within IMD 200. Power source 224 may include any one or more of a plurality of different battery types, such as nickel cadmium batteries and lithium ion batteries.

In accordance with the techniques of the disclosure, telemetry circuitry 208 may process a request from external programmer 150 to cause processing circuitry 210 to provide therapy at an updated intensity level. For example, intensity level unit 245 of processing circuitry 210 may adjust one or more of an amplitude, a pulse width, and/or a frequency of electrical stimulation pulses provided to a patient of in response to the request.

Figure 3:
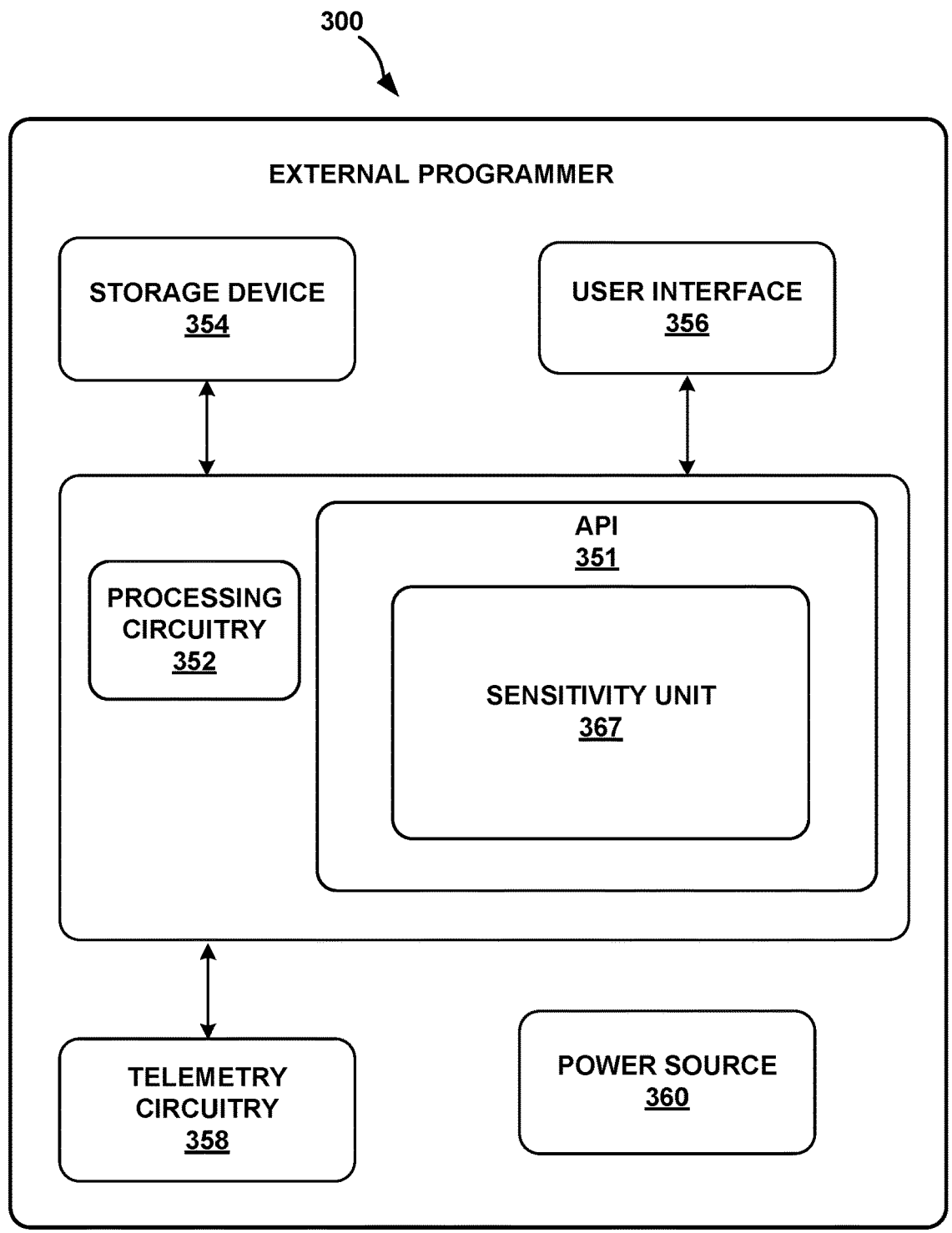
FIG. 3 is a block diagram illustrating an example of an external programmer suitable for use with the IMD of FIG. 2, in accordance with one or more techniques of this disclosure.

FIG. 3 is a block diagram illustrating an example configuration of components of an example external programmer 300. External programmer 300 may be an example of external programmer 150 (e.g., an external patient programmer or an external clinician programmer) of FIG. 1. Although external programmer 300 may generally be described as a hand-held device, external programmer 300 may be a larger portable device or a more stationary device. In addition, in other examples, external programmer 300 may be included as part of an external charging device or include the functionality of an external charging device. As illustrated in FIG. 3, external programmer 300 may include processing circuitry 352, storage device 354, user interface 356, telemetry circuitry 358, and power source 360. Storage device 354 may store instructions that, when executed by processing circuitry 352, cause processing circuitry 352 and external programmer 300 to provide the functionality ascribed to external programmer 300 throughout this disclosure. Each of these components, circuitry, or modules, may include electrical circuitry that is configured to perform some, or all of the functionality described herein. For example, processing circuitry 352 may include one or more processors, such as, one or more microprocessors, DSPs, ASICs, FPGAs, or any other equivalent integrated or discrete logic circuitry, as well as any combinations of such components, configured to perform the processes discussed with respect to processing circuitry 352. External programmer 300 may represent a patient programmer, clinician programmer, or another device.

In general, external programmer 300 includes any suitable arrangement of hardware, alone or in combination with software and/or firmware, to perform the techniques attributed to external programmer 300, and processing circuitry 352, user interface 356, and telemetry circuitry 358 of external programmer 300. In various examples, external programmer 300 may include one or more processors, such as one or more microprocessors, DSPs, ASICs, FPGAs, or any other equivalent integrated or discrete logic circuitry, as well as any combinations of such components. External programmer 300 also, in various examples, may include a storage device 354, such as RAM, ROM, PROM, EPROM, EEPROM, flash memory, a hard disk, a CD-ROM, including executable instructions for causing the one or more processors to perform the actions attributed to them. Moreover, although processing circuitry 352 and telemetry circuitry 358 are described as separate modules, in some examples, processing circuitry 352 and telemetry circuitry 358 are functionally integrated. In some examples, processing circuitry 352 and telemetry circuitry 358 correspond to individual hardware units, such as ASICs, DSPs, FPGAs, or other hardware units.

Storage device 354 (e.g., a storage device) may store instructions that, when executed by processing circuitry 352, cause processing circuitry 352 and external programmer 300 to provide the functionality ascribed to external programmer 300 throughout this disclosure. For example, storage device 354 may include instructions that cause processing circuitry 352 to obtain a parameter set from memory or receive user input and send a corresponding command to IMD 110, or instructions for any other functionality. In addition, storage device 354 may include a plurality of programs, where each program includes a parameter set that defines therapy stimulation or control stimulation. Storage device 354 may also store data received from a medical device (e.g., IMD 110). For example, storage device 354 may store data recorded at a sensing module of the medical device, and storage device 354 may also store data from one or more sensors of the medical device.

Processing circuitry 352 may be configured to control IMD 110 with a program to provide stimulation. For example, processing circuitry 352 may automatically or semi-automatically set or adjust programs at IMD 110 by transmitting, with telemetry circuitry 358, instructions to IMD 110. For instance, in response to a change (e.g., a change indicated by user input, a change sensed by IMD 110, etc.) in activity of a patient (e.g., standing, walking, voiding, etc.), processing circuitry 352 may automatically or semi-automatically set or adjust programs at IMD 110. For instance, processing circuitry 352 may, in response to determining that the patient would not like to void, output instructions to IMD 110 to use a first group stored at IMD 110 for controlled voiding. In this instance, processing circuitry 352 may, in response to determining that the patient would like to void, output instructions to IMD 110 to use a new group or program stored at IMD 110 for controlled voiding.

User interface 356 may include a button or keypad, lights, a speaker for voice commands, a display, such as a liquid crystal (LCD), light-emitting diode (LED), or organic light-emitting diode (OLED). In some examples the display includes a touch screen. User interface 356 may be configured to display any information related to the delivery of electrical stimulation. User interface 356 may also receive user input (e.g., indication of when the patient perceives a stimulation pulse) via user interface 356. The input may be, for example, in the form of pressing a button on a keypad or selecting an icon from a touch screen. The input may request starting or stopping electrical stimulation, the input may request a new spatial electrode pattern or a change to an existing spatial electrode pattern, of the input may request some other change to the delivery of electrical stimulation.

Telemetry circuitry 358 may support wireless communication between the medical device and external programmer 300 under the control of processing circuitry 352. Telemetry circuitry 358 may also be configured to communicate with another computing device via wireless communication techniques, or direct communication through a wired connection. In some examples, telemetry circuitry 358 provides wireless communication via an RF or proximal inductive medium. In some examples, telemetry circuitry 358 includes an antenna, which may take on a variety of forms, such as an internal or external antenna.

Examples of local wireless communication techniques that may be employed to facilitate communication between external programmer 300 and IMD 110 include RF communication according to the 802.11 or Bluetooth® specification sets or other standard or proprietary telemetry protocols. In this manner, other external devices may be capable of communicating with external programmer 300 without needing to establish a secure wireless connection. As described herein, telemetry circuitry 358 may be configured to transmit a spatial electrode movement pattern or other stimulation parameter values to IMD 110 for delivery of electrical stimulation therapy.

Power source 360 is configured to deliver operating power to the components of external programmer 300. Power source 360 may include a battery and a power generation circuit to produce the operating power. In some examples, the battery is rechargeable to allow extended operation. Recharging may be accomplished by electrically coupling power source 360 to a cradle or plug that is connected to an alternating current (AC) outlet. In addition, recharging may be accomplished through proximal inductive interaction between an external charger and an inductive charging coil within external programmer 300. In other examples, traditional batteries (e.g., nickel cadmium or lithium ion batteries) may be used. In addition, external programmer 300 may be directly coupled to an alternating current outlet to operate.

Processing circuitry 352 may implement API 351 to facilitate the control of IMD 110. API 351 may include sensitivity unit 367. Sensitivity unit 367 may be configured to determine a sensitivity level for adjustment. For instance, sensitivity unit 367 may increase or decrease the amount by which the intensity changes per input from patient 105. As an example, for a first sensitivity level, turning the therapy knob by one notch causes the intensity level to increase by a first amount. For a second sensitivity level, turning the therapy knob by one notch causes the intensity level to increase by a second, different amount.

For example, sensitivity unit 367 may receive an indication of a patient providing an input to adjust an intensity setting related to therapy provided to the patient. As described in further detail below, sensitivity unit 367 may determine a sensitivity level based on one or more of a current activity level for the patient, an amount of sleep during a period of time for patient 105, a sleep position during a period of time for patient 105, a set of previous therapy parameter adjustments, a pain rating, a set of physiological signals (e.g., ECAP and/or LFP), or a mode of external programmer (e.g., training or trial mode, or chronic mode). Sensitivity unit 367 may determine an updated intensity level for the intensity setting based on the sensitivity level and the input to adjust the intensity setting. In some examples, sensitivity unit 367 may determine the updated intensity level to be within a preconfigured safety range of intensity levels. For example, a clinician may set the preconfigured safety range of intensity levels using a remote device. Sensitivity unit 367 may cause a medical device (e.g., IMD 110) to provide therapy at the updated intensity level. While external programmer 300 is described below as determining a sensitivity level, any combination of external programmer 300, IMD 110, a remote device, or one or more processors may be configured to determine the sensitivity level.

Sensitivity unit 367 may determine a sensitivity level for adjustment based on a mode of external programmer 300 or an efficacy of therapy. For example, sensitivity unit 367 may determine the sensitivity level for adjustment based on one or more of a current activity level for the patient, an amount of sleep during a period of time for patient 105, a sleep position during a period of time for patient 105, a set of previous therapy parameter adjustments, a pain rating, a set of physiological signals (e.g., ECAP and/or LFP), or a mode of external programmer (e.g., training or trial mode, or chronic mode).

Sensitivity unit 367 may determine a current activity level for the patient. For example, sensitivity unit 367 may determine the activity level based on sensed condition information generated by medical device 110. For instance, sensors 222 may include one or more accelerometers. In this example, sensitivity unit 367 may receive the current activity level and/or acceleration information indicated by the sensed condition information via telemetry circuitry 208 and telemetry circuitry 358. Sensitivity unit 367 may determine the current activity level using the acceleration information generated by sensors 222. Sensitivity unit 367 may receive an input indicating the activity level. For example, sensitivity unit 367 may receive an indication of the current activity level from patient 105 via user interface 356.

Sensitivity unit 367 may determine the sensitivity level for adjustment based on the current activity level. For example, sensitivity unit 367 may increase the sensitivity level for adjustment in response to determining that the current activity level is less than a baseline activity level for the patient and decrease the sensitivity level for adjustment in response to determining that the current activity level is greater than the baseline activity level for the patient. In some examples, sensitivity unit 367 may increase the sensitivity level for adjustment in response to determining that the current activity level is greater than a baseline activity level for the patient and decrease the sensitivity level for adjustment in response to determining that the current activity level is less than the baseline activity level for the patient. The baseline activity level may be static or rolling. In some examples, the baseline activity level may be configured by a clinician. For instance, a clinician may select how long to use a baseline activity level with current activity level. In some examples, the clinician may select a tolerance (e.g., more than 20% increase) added to a sensed or determined baseline activity level.

Sensitivity unit 367 may determine the sensitivity level based on an amount of sleep (e.g., a number of minutes and/or a number of hours) during a period of time (e.g., a day, a week, or a month) for patient 105. For example, sensitivity unit 367 may determine an amount of sleep during a period of time for the patient. Sensitivity unit 367 may determine the amount of sleep based on sensed condition information generated by medical device 110. For instance, sensors 222 may include one or more accelerometers. In this example, sensitivity unit 367 may receive the amount of sleep and/or acceleration information indicated by the sensed condition information via telemetry circuitry 208 and telemetry circuitry 358. Sensitivity unit 367 may determine the amount of sleep using the acceleration information generated by sensors 222. Sensitivity unit 367 may receive an input indicating the amount of sleep. For example, sensitivity unit 367 may receive an indication of the amount of sleep from patient 105 via user interface 356.

Sensitivity unit 367 may determine the sensitivity level for adjustment based on the amount of sleep. For example, sensitivity unit 367 may increase the sensitivity level for adjustment in response to determining that the amount of sleep is less than a baseline sleep level for the patient and decrease the sensitivity level for adjustment in response to determining that the amount of sleep is greater than the baseline sleep level for the patient. In some examples, sensitivity unit 367 may increase the sensitivity level for adjustment in response to determining that the amount of sleep is greater than a baseline sleep level for the patient and decrease the sensitivity level for adjustment in response to determining that the amount of sleep is less than the baseline sleep level for the patient.

Sensitivity unit 367 may determine the sensitivity level for adjustment based on the time of day. For example, sensitivity unit 367 may increase the sensitivity level for adjustment in response to determining that the time of day is during sleep hours and decrease the sensitivity level for adjustment in response to determining that the time of day is not during sleep hours. In some examples, sensitivity unit 367 may increase the sensitivity level for adjustment in response to determining that the time of day is not during sleep hours and decrease the sensitivity level for adjustment in response to determining that the time of day is during sleep hours. The time of day is during sleep hours may be configurable, by patient 105 and/or by a clinician.

Sensitivity unit 367 may determine the sensitivity level based on a sleep position (e.g., a side, front, or back) during a period of time (e.g., a day, a week, or a month) for patient 105. For example, sensitivity unit 367 may determine an amount of sleep during a period of time for the patient. Sensitivity unit 367 may determine the sleep position based on sensed condition information generated by medical device 110. For instance, sensors 222 may include one or more accelerometers. In this example, sensitivity unit 367 may receive the sleep position and/or acceleration information indicated by the sensed condition information via telemetry circuitry 208 and telemetry circuitry 358. Sensitivity unit 367 may receive an input indicating a sleep position. For example, sensitivity unit 367 may receive an indication of the sleep position from patient 105 via user interface 356. Sensitivity unit 367 may determine the sensitivity level for adjustment based on the sleep position.

For example, sensitivity unit 367 may increase the sensitivity level for adjustment in response to determining that patient 105 has slept in a first sleep position during the period of time and decrease the sensitivity level for adjustment in response to determining that patient 105 has slept in a second sleep position during the period of time.

Sensitivity unit 367 may determine the sensitivity level based on a set of previous therapy parameter adjustments during a period of time (e.g., a number of minutes and/or a number of hours) for patient 105. For example, sensitivity unit 367 may determine the number of parameter adjustments during the period of time. Sensitivity unit 367 may determine the sensitivity level for adjustment based on the number of parameter adjustments during the period of time. For example, sensitivity unit 367 may increase the sensitivity level for adjustment in response to determining that the number of parameter adjustments during the period of time is less than a baseline number of changes for patient 105 and decrease the sensitivity level for adjustment in response to determining that the number of parameter adjustments during the period of time is greater than the baseline number of changes for patient 105.

Sensitivity unit 367 may determine the sensitivity level based on a pain rating during a period of time (e.g., a number of minutes and/or a number of hours) for patient 105. For example, sensitivity unit 367 may receive an input indicating a pain rating from patient 105. Sensitivity unit 367 may determine the sensitivity level for adjustment based on the pain rating. For example, sensitivity unit 367 may increase the sensitivity level for adjustment in response to determining that the pain rating during the period of time is less than a baseline pain rating for patient 105 and decrease the sensitivity level for adjustment in response to determining that the pain rating during the period of time is greater than the baseline pain rating for patient 105.

Sensitivity unit 367 may determine the sensitivity level for adjustment based a set of physiological signals. For example, sensitivity unit 367 may determine one or more of evoked compound action potential (ECAP) or local field potential (LFP) generated by medical device 110. In this example, sensitivity unit 367 may receive the set of physiological signals via telemetry circuitry 208 and telemetry circuitry 358. Sensitivity unit 367 may determine the sensitivity level for adjustment based on the set of physiological signals.

The architecture of external programmer 300 illustrated in FIG. 3 is shown as an example. The techniques as set forth in this disclosure may be implemented in the example external programmer 300 of FIG. 3, as well as other types of systems not described specifically herein. Nothing in this disclosure should be construed so as to limit the techniques of this disclosure to the example architecture illustrated by FIG. 3.

Figure 4:
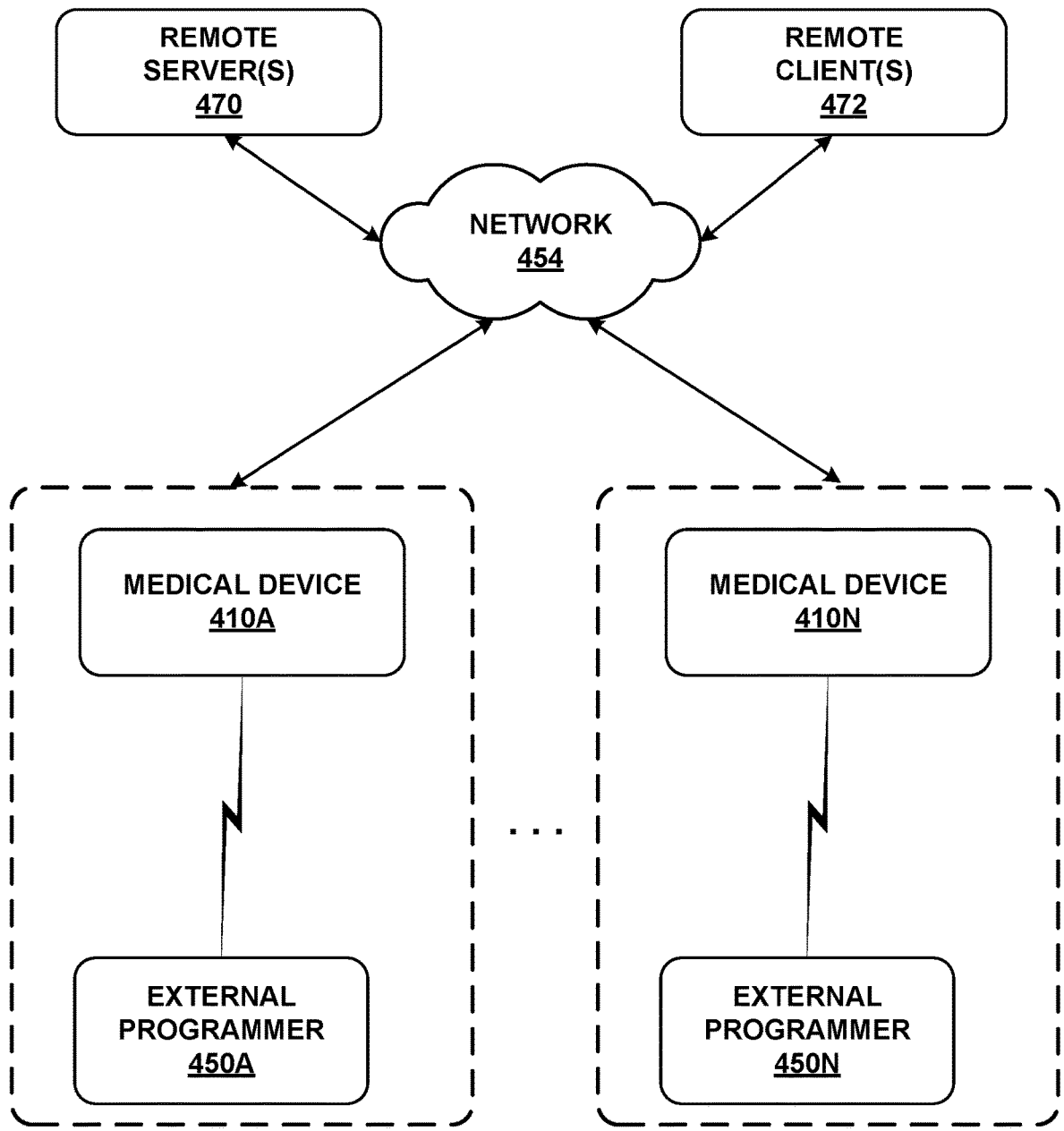
FIG. 4 is a block diagram illustrating an example of one or more remote servers and one or more remote clients suitable for use with the IMD of FIG. 1, in accordance with one or more techniques of this disclosure.

FIG. 4 is a block diagram illustrating an example of one or more remote servers 470 (referred to herein as "remote server 470") and one or more remote clients 472 (referred to herein as "remote clients 472") suitable for use with the IMD of FIG. 1, in accordance with one or more techniques of this disclosure. Remote server 470 may represent a cloud computing infrastructure, such as, for example a cloud or web interface. Remote client 472 may represent a clinician device geographically remote from external programmer 150 and/or IMD 110. In some examples, remote server 470 may work with remote client 472. For instance, remote server 470 may store data or at least partially process data for remote client 472. Remote client 472 may be used by a health professional at a doctor's office and the patient and IMD 110 may be at a home of the patient. Remote server 470 and/or remote client 472 may be referred to herein as a remote device. Network 454 may comprise one or more wired (e.g., Ethernet) and/or wireless networks (e.g., Wi-Fi™, Bluetooth™, Zigbee™, IEEE 802.11, etc.). In some examples, network 454 may comprise the Internet. While the previous examples refer to remote client 472 as performing various processes, any combination of medical devices, external programmers 450, remote server 470, or remote client 472 may perform such processes. Moreover, remote client 472 (or any combination of medical devices, external programmers 450, remote server 470, or remote client 472) may perform the processes described as being performed by external programmer 150 of FIG. 1 and/or external programmer 300 of FIG. 3.

A remote device (e.g., remote server 470 and/or remote client 472) may be configured to control IMD 110 with a program or a group of programs to provide stimulation. For example, the remote device may automatically or semi-automatically set or adjust programs at IMD 110. For instance, in response to a change in activity of a patient (e.g., standing, walking, voiding, etc.), the remote device may automatically or semi-automatically set or adjust programs at IMD 110. For instance, the remote device may receive sensor information or user input information from IMD 110 or external programmer 150 via the network 454 that indicates a change in activity of the patient. While the following examples refer to remote client 472 as performing processes directed to identifying problem patients, initiating a diagnostic test, prioritizing a delivery of data, scheduling a virtual appointments, any combination of medical devices 410A-410N (collectively, "medical devices 410"), external programmers 450A-450N (collectively, "external programmers 450"), remote server 470, or remote client 472 may perform processes described herein directed to identifying problem patients, initiating a diagnostic test, prioritizing a delivery of data, scheduling a virtual appointments.

In accordance with the techniques of the disclosure, remote client 472 may be configured to help a patient provide input to adjust a sensitivity of an intensity setting set by a clinician. While external programmer 450A is used as an example external programmer, any one of external programmers 150 may be used to adjust the sensitivity of the intensity setting. For example, remote client 472 may, with external programmer 450A, provide a "therapy knob" that adjusts the intensity setting based on one or more adjustment parameters (e.g., a mode of the external device, an efficacy of therapy, etc.). Intensity may be a function of amplitude, pulse width, and/or frequency.

For example, if external programmer 450A is in a training or trial mode, remote client 472 may determine that an input to change an intensity using the therapy knob (e.g., one notch) may result in larger adjustments than when the external device is in chronic mode. In some examples, remote client 472 may set the sensitivity of the therapy knob based on an activity level of the patient. Remote client 472 may instruct medical device 410 to provide therapy using the intensity setting.

Remote client 472 may set a sensitivity of the therapy knob based on an efficacy of therapy. For DBS, remote client 472 may determine the efficacy of therapy based on an amount of tremor, ambulation, and/or open and closed fist range. In this way, the system may help to provide patient control measures that simplify or make changes to a therapy easier for a patient, which may improve a therapy provided to the patient. Moreover, patient control measures may reduce a number of times that a clinician sets an intensity level for therapy, which may help to reduce an amount of time a clinician spends configuring medical devices.

Although shown as separate entities, in some examples, functionality may be distributed differently than that shown in FIG. 4. For example, remote server 470 and remote client 472 may be the same system. While the previous examples refer to remote client 472 as performing various processes, any combination of medical devices, external programmers 450, remote server 470, or remote client 472 may perform such processes.

Figure 5:
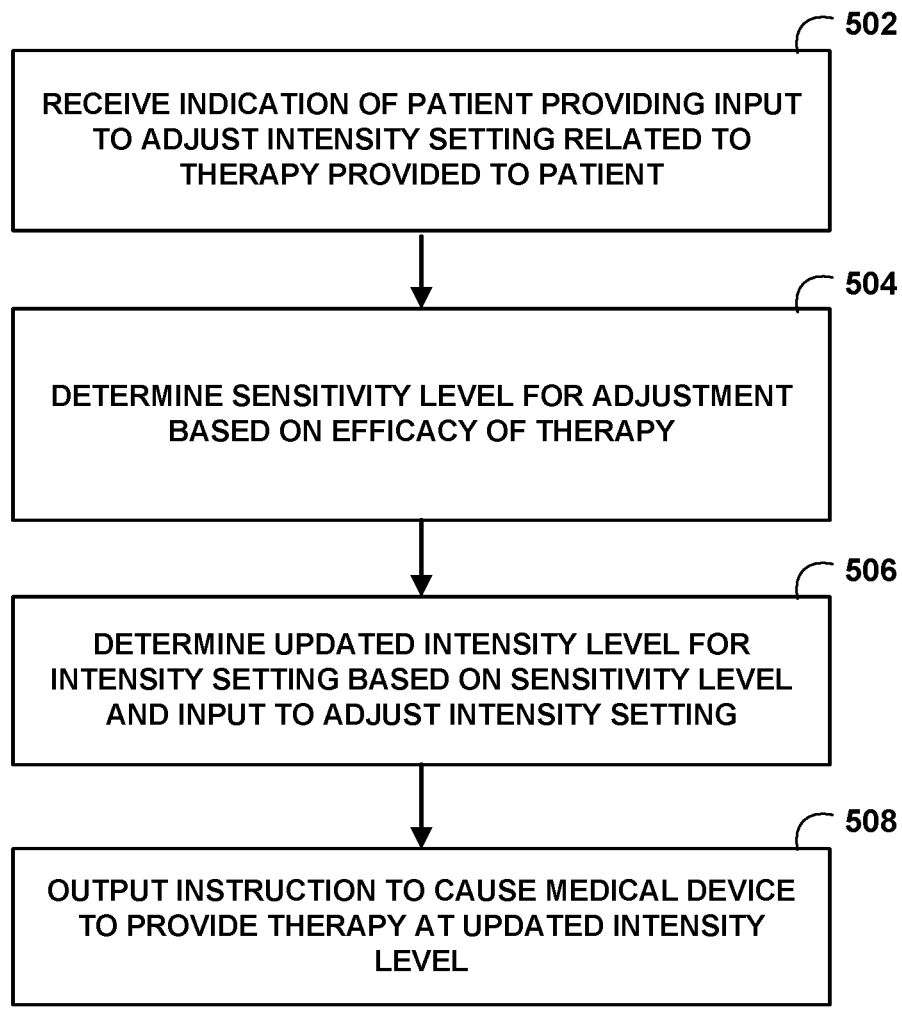
FIG. 5 is a flow diagram illustrating a process for determining a sensitivity level for adjustment, in accordance with one or more techniques of this disclosure.

FIG. 5 is a flow diagram illustrating a process for determining a sensitivity level for adjustment, in accordance with one or more techniques of this disclosure. FIG. 5 is discussed with reference to FIGS. 1-4 for example purposes only. In the following example, external programmer 150 performs 502-508 of FIG. 5. However, in other examples, other devices may perform the process of FIG. 5 as explained in further detail below. In the following examples, IMD 110 is used as a medical device. However, in some examples, an external medical device may be used instead of IMD 110.

External programmer 150 may receive an indication of a patient providing an input to adjust an intensity setting related to therapy provided to the patient (502). External programmer 150 may determine a sensitivity level for adjustment based on an efficacy of therapy (504). For example, external programmer 150 may determine a sensitivity level for adjustment based on one or more of a current activity level for the patient, an amount of sleep during a period of time for patient 105, a time of day, a sleep position during a period of time for patient 105, a set of previous therapy parameter adjustments, a pain rating, a set of physiological signals (e.g., ECAP and/or LFP). In some examples, external programmer 150 may determine a sensitivity level for adjustment based on a mode of external programmer (e.g., training or trial mode, or chronic mode). External programmer may determine an updated intensity level for the intensity setting based on the sensitivity level and the input to adjust the intensity setting (506). External programmer 150 may output an instruction to cause a medical device (e.g., IMD 110) to provide therapy at the updated intensity level (508).

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over as one or more instructions or code on a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processors to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transitory media, but are instead directed to non-transitory, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Instructions may be executed by one or more processors, such as one or more digital signal processors (DSPs), general purpose microprocessors, application specific integrated circuits (ASICs), field programmable gate arrays (FPGAs), or other equivalent integrated or discrete logic circuitry. Accordingly, the terms "processor" and "processing circuitry," as used herein may refer to any of the foregoing structures or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a codec hardware unit or provided by a collection of interoperative hardware units, including one or more processors as described above, in conjunction with suitable software and/or firmware.

The following numbered clauses illustrate one or more aspects of the devices and techniques described in this disclosure.

Clause 1. A system for selecting a sensitivity level for adjusting an intensity setting for therapy provided to a patient, the system comprising one or more processors and one or more processors coupled to the memory, wherein the one or more processors are configured to: receive an indication of an input to adjust an intensity setting related to the therapy provided to the patient; determine a sensitivity level for adjustment of the intensity setting based on an efficacy of the therapy provided to the patient; determine an updated intensity level for the intensity setting based on the sensitivity level and the input to adjust the intensity setting; and output an instruction to cause a medical device to provide the therapy at the updated intensity level.

Clause 2. The system of clause 1, wherein, to determine the sensitivity level, the one or more processors are configured to: determine a current activity level for the patient; and determine the sensitivity level for adjustment based on the current activity level and the efficacy of the therapy provided to the patient.

Clause 3. The system of clause 2, wherein, to determine the current activity level for the patient, the one or more processors are configured to determine the activity level based on sensed condition information generated by the medical device.

Clause 4. The system of any combination of clauses 2-3, wherein, to determine the current activity level for the patient, the one or more processors are configured to receive, at an external programmer associated with the medical device, an input indicating the activity level.

Clause 5. The system of any combination of clauses 2-4, wherein, to determine the sensitivity level, the one or more processors are configured to: increase the sensitivity level for adjustment of the intensity setting, from a current sensitivity level, in response to determining that the current activity level is less than a baseline activity level for the patient; or decrease the sensitivity level for adjustment of the intensity setting, from the current sensitivity level, in response to determining that the current activity level is greater than the baseline activity level for the patient.

Clause 6. The system of any combination of clauses 2-4, wherein, to determine the sensitivity level, the one or more processors are configured to: increase the sensitivity level for adjustment of the intensity setting, from a current sensitivity level, in response to determining that the current activity level is greater than a baseline activity level for the patient; and decrease the sensitivity level for adjustment of the intensity setting, from the current sensitivity level, in response to determining that the current activity level is less than the baseline activity level for the patient.

Clause 7. The system of any combination of clauses 1-6, wherein, to determine the sensitivity level, the one or more processors are configured to: determine an amount of sleep during a period of time for the patient; and determine the sensitivity level for adjustment based on the amount of sleep and the efficacy of the therapy provided to the patient.

Clause 8. The system of clause 7, wherein, to determine the amount of sleep, the one or more processors are configured to determine the amount of sleep based on sensed condition information generated by the medical device.

Clause 9. The system of any combination of clauses 7-8, wherein, to determine the amount of sleep, the one or more processors are configured to receive, at an external programmer associated with the medical device, an input indicating the amount of sleep.

Clause 10. The system of any combination of clauses 1-9, wherein, to determine the sensitivity level, the one or more processors are configured to: determine a sleep position during a period of time for the patient; and determine the sensitivity level for adjustment based on the sleep position and the efficacy of the therapy provided to the patient.

Clause 11. The system of clause 10, wherein, to determine the sleep position, the one or more processors are configured to determine the sleep position based on sensed condition information generated by the medical device.

Clause 12. The system of any combination of clauses 1-11, wherein, to determine the sensitivity level, the one or more processors are configured to: determine a set of previous therapy parameter adjustments during a period of time for the patient; and determine the sensitivity level for adjustment based on the set of previous therapy parameter adjustments and the efficacy of the therapy provided to the patient.

Clause 13. The system of any combination of clauses 1-12, wherein, to determine the sensitivity level, the one or more processors are configured to: receive, at an external programmer associated with the medical device, an input indicating a pain rating; and determine the sensitivity level for adjustment based on the pain rating and the efficacy of the therapy provided to the patient.

Clause 14. The system of any combination of clauses 1-13, wherein, to determine the sensitivity level, the one or more processors are configured to: sense, with the medical device, a set of physiological signals; and determine the sensitivity level for adjustment based on the set of physiological signals and the efficacy of the therapy provided to the patient.

Clause 15. The system of clause 14, wherein the set of physiological signals comprises one or more of evoked compound action potential (ECAP) or local field potential (LFP).

Clause 16. The system of any combination of clauses 1-15, wherein, to determine the updated intensity level for the intensity setting, the one or more processors are configured to determine the updated intensity level to be within a preconfigured safety range of intensity levels.

Clause 17. The system of any combination of clauses 1-16, wherein to receive the indication of the patient input, the one or more processors are configured to receive the indication of the patient input at an external programmer associated with the medical device.

Clause 18. The system of any combination of clauses 1-17, wherein the medical device is configured to provide one or more of deep brain stimulation (DBS), spinal cord stimulation (SCS), sacral neuromodulation (SNS), or targeted drug delivery (TDD).

Clause 19. A method for selecting a sensitivity level for adjusting an intensity setting for therapy provided to a patient, the method comprising: receiving, by one or more processors, an indication of an input to adjust an intensity setting related to the therapy provided to the patient; determining, by the one or more processors, a sensitivity level for adjustment of the intensity setting based on an efficacy of the therapy provided to the patient; determining, by the one or more processors, an updated intensity level for the intensity setting based on the sensitivity level and the input to adjust the intensity setting; and outputting, by the one or more processors, an instruction to cause a medical device to provide the therapy at the updated intensity level.

Clause 20. An external programmer for adjusting an intensity setting for therapy provided to a patient, the external programmer comprising one or more processors configured to: receive an indication of an input to adjust an intensity setting related to the therapy provided to the patient; determine a sensitivity level for adjustment of the intensity setting based on an efficacy of the therapy provided to the patient; determine an updated intensity level for the intensity setting based on the sensitivity level and the input to adjust the intensity setting; and output an instruction to cause a medical device to provide the therapy at the updated intensity level.

What is claimed is:

1. A system for selecting a sensitivity level for adjusting an intensity setting for therapy provided to a patient, the system comprising memory and one or more processors coupled to the memory, wherein the one or more processors are configured to:
   receive an indication of an input to adjust the intensity setting for the therapy provided to the patient;
   determine a sensitivity level for adjustment of the intensity setting based on an efficacy of the therapy provided to the patient, wherein the sensitivity level indicates an amount by which an intensity of the intensity setting changes;
   determine an updated intensity level for the intensity setting based on the sensitivity level and the input to adjust the intensity setting, wherein to determine the updated intensity level, the one or more processors are configured to increase or decrease the intensity level for the intensity setting by the amount indicated by the sensitivity level; and
   output an instruction to cause a medical device to provide the therapy at the updated intensity level.

2. The system of claim 1, wherein, to determine the sensitivity level, the one or more processors are configured to:
   determine a current activity level for the patient; and
   determine the sensitivity level for adjustment based on the current activity level and the efficacy of the therapy provided to the patient.

3. The system of claim 2, wherein, to determine the current activity level for the patient, the one or more processors are configured to determine the activity level based on sensed condition information generated by the medical device.

4. The system of claim 2, wherein, to determine the current activity level for the patient, the one or more processors are configured to receive, at an external programmer associated with the medical device, an input indicating the activity level.

5. The system of claim 2, wherein, to determine the sensitivity level, the one or more processors are configured to:
   increase the sensitivity level for adjustment of the intensity setting, from a current sensitivity level, in response to determining that the current activity level is less than a baseline activity level for the patient; or
   decrease the sensitivity level for adjustment of the intensity setting, from the current sensitivity level, in response to determining that the current activity level is greater than the baseline activity level for the patient.

6. The system of claim 2, wherein, to determine the sensitivity level, the one or more processors are configured to:
   increase the sensitivity level for adjustment of the intensity setting, from a current sensitivity level, in response to determining that the current activity level is greater than a baseline activity level for the patient; and
   decrease the sensitivity level for adjustment of the intensity setting, from the current sensitivity level, in response to determining that the current activity level is less than the baseline activity level for the patient.

7. The system of claim 1, wherein, to determine the sensitivity level, the one or more processors are configured to:
   determine an amount of sleep during a period of time for the patient; and
   determine the sensitivity level for adjustment based on the amount of sleep and the efficacy of the therapy provided to the patient.

8. The system of claim 7, wherein, to determine the amount of sleep, the one or more processors are configured to determine the amount of sleep based on sensed condition information generated by the medical device.

9. The system of claim 7, wherein, to determine the amount of sleep, the one or more processors are configured to receive, at an external programmer associated with the medical device, an input indicating the amount of sleep.

10. The system of claim 1, wherein, to determine the sensitivity level, the one or more processors are configured to:
determine a sleep position during a period of time for the patient; and
determine the sensitivity level for adjustment based on the sleep position and the efficacy of the therapy provided to the patient.

11. The system of claim 10, wherein, to determine the sleep position, the one or more processors are configured to determine the sleep position based on sensed condition information generated by the medical device.

12. The system of claim 1, wherein, to determine the sensitivity level, the one or more processors are configured to:
determine a set of previous therapy parameter adjustments during a period of time for the patient; and
determine the sensitivity level for adjustment based on the set of previous therapy parameter adjustments and the efficacy of the therapy provided to the patient.

13. The system of claim 1, wherein, to determine the sensitivity level, the one or more processors are configured to:
receive, at an external programmer associated with the medical device, an input indicating a pain rating; and
determine the sensitivity level for adjustment based on the pain rating and the efficacy of the therapy provided to the patient.

14. The system of claim 1, wherein, to determine the sensitivity level, the one or more processors are configured to:
sense, with the medical device, a set of physiological signals; and
determine the sensitivity level for adjustment based on the set of physiological signals and the efficacy of the therapy provided to the patient.

15. The system of claim 14, wherein the set of physiological signals comprises one or more of evoked compound action potential (ECAP) or local field potential (LFP).

16. The system of claim 1, wherein, to determine the updated intensity level for the intensity setting, the one or more processors are configured to determine the updated intensity level to be within a preconfigured safety range of intensity levels.

17. The system of claim 1, wherein to receive the indication of the patient input, the one or more processors are configured to receive the indication of the patient input at an external programmer associated with the medical device.

18. The system of claim 1, wherein the medical device is configured to provide one or more of deep brain stimulation (DBS), spinal cord stimulation (SCS), sacral neuromodulation (SNS), or targeted drug delivery (TDD).

19. A method for selecting a sensitivity level for adjusting an intensity setting for therapy provided to a patient, the method comprising:
receiving, by one or more processors, an indication of an input to adjust the intensity setting for the therapy provided to the patient;
determining, by the one or more processors, a sensitivity level for adjustment of the intensity setting based on an efficacy of the therapy provided to the patient, wherein the sensitivity level indicates an amount by which an intensity of the intensity setting changes;
determining, by the one or more processors, an updated intensity level for the intensity setting based on the sensitivity level and the input to adjust the intensity setting, wherein determining the updated intensity level comprises increasing or decreasing the intensity level for the intensity setting by the amount indicated by the sensitivity level; and
outputting, by the one or more processors, an instruction to cause a medical device to provide the therapy at the updated intensity level.

20. An external programmer for adjusting an intensity setting for therapy provided to a patient, the external programmer comprising one or more processors and configured to:
receive an indication of an input to adjust the intensity setting for the therapy provided to the patient;
determine a sensitivity level for adjustment of the intensity setting based on an efficacy of the therapy provided to the patient, wherein the sensitivity level indicates an amount by which an intensity of the intensity setting changes;
determine an updated intensity level for the intensity setting based on the sensitivity level and the input to adjust the intensity setting, wherein to determine the updated intensity level, the external programmer is configured to increase or decrease the intensity level for the intensity setting by the amount indicated by the sensitivity level; and
output an instruction to cause a medical device to provide the therapy at the updated intensity level.

* * * * *